United States Patent [19]

Saito et al.

[11] 4,343,722

[45] Aug. 10, 1982

[54] PROCESS FOR PRODUCING CATALYST

[75] Inventors: Masao Saito, Niigata; Yuuzi Onda, Kawasaki; Yuko Murayama, Niigata, all of Japan

[73] Assignee: Mitsubishi Gas Chemical Company, Inc., Tokyo, Japan

[21] Appl. No.: 249,506

[22] Filed: Mar. 31, 1981

[30] Foreign Application Priority Data

Apr. 3, 1980 [JP] Japan ................................. 55-44427

[51] Int. Cl.³ ......................... B01J 31/12; B01J 31/02
[52] U.S. Cl. ............................... 252/431 N; 252/428; 564/490
[58] Field of Search ........................... 252/431 N, 428

[56] References Cited

U.S. PATENT DOCUMENTS

| | | | |
|---|---|---|---|
| 2,644,842 | 7/1953 | Hager | 260/583 |
| 2,666,748 | 1/1954 | Arthur et al. | 252/431 N |
| 3,427,256 | 2/1969 | Milgrom | 252/428 |

*Primary Examiner*—Arthur P. Demers
*Attorney, Agent, or Firm*—Armstrong, Nikaido, Marmelstein & Kubovcik

[57] ABSTRACT

A catalyst for hydrogenation of nitriles with a high activity is produced by heating dicobalt octacarbonyl together with an aromatic nitrile at a temperature of 100°–200° C. in the absence of oxygen gas.

8 Claims, No Drawings

PROCESS FOR PRODUCING CATALYST

This invention relates to a process for producing a novel cobalt catalyst for hydrogenation of nitriles.

Cobalt catalysts supported on an inorganic porous carrier such as diatomaceous earth or the like are well known hitherto, and are extensively used as catalyst for use in the hydrogenation of aliphatic and aromatic nitriles.

Such hitherto known cobalt catalysts, i.e. reduced cobalt catalysts, are generally prepared in the following manner. An aqueous solution of water-soluble cobalt salt such as cobalt nitrate, or cobalt sulfate is admixed with a precipitant for cobalt salt, such as sodium carbonate, sodium bicarbonate, sodium hydroxide, ammonium carbonate or the like, it necessary, after a carrier has been immersed in the solution to precipitate the water-soluble cobalt salt in the form of basic cobalt carbonate or cobalt hydroxide. Subsequently, the precipitate is aged, washed with water and dried, and then is heated at 300°–500° C. to thermally decompose the basic cobalt salt to cobalt oxide and then reduced with hydrogen at 300°–500° C. to obtain a reduced cobalt catalyst. The resulting catalyst can be in a powdery or shaped form.

In producing the catalyst, a metallic component such as chromium, copper, manganese, molybdenum, magnesium or the like can be used as a promotor, and a water-soluble salt of the metallic promoter component such as nitrate or sulfate is simultaneously added to the aqueous solution of the water-soluble cobalt salt.

The reduced cobalt catalyst must be produced by hydrogen reduction of cobalt oxide at a high temperature, and the reduced cobalt catalyst once obtained by the hydrogen reduction will undergo considerable decrease in activity or heat release or ignition, when it comes in contact with air, particularly oxygen. Thus, its handling requires the greatest care and is troublesome.

The so-called stabilized cobalt catalyst, which has been made easy to handle by oxidizing and stabilizing only the surface of the reduced cobalt, once obtained by hydrogen reduction at the high temperature, with carbon dioxide, air or the like, can be handled without ignition in the air. However, before the hydrogenation reaction it must be again reduced with hydrogen, though at a lower temperature than that for the reduction of cobalt oxide. The procedures for using it or producing it is complicated.

The present inventors have found an entirely novel process for producing a cobalt catalyst having a high activity and simple to handle or to use, free from the disadvantages in the production and the complicatedness in use of the hitherto known reduced cobalt catalysts.

The inventors have found that the precipitate formed by heating dicobalt octacarbonyl as a starting material for catalyst together with an aromatic nitrile at a temperature of 100°–200° C. in a system containing no oxygen has a very high activity in the hydrogenation of nitriles, and have established the present invention.

The present catalyst is produced by heating a solution of dicobalt octacarbonyl and an aromatic nitrile in a solvent at a temperature of 100°–200° C. in a system containing no oxygen.

As the aromatic nitrile, benzonitrile, phthalonitrile, isophthalonitrile, terephthalonitrile, etc. can be used.

As the solvent, those capable of dissolving dicobalt octacarbonyl and aromatic nitrile and having a boiling point of 100° C. or higher are preferable, and include hydrocarbons such as toluene, xylene, mesitylene, etc.; amide solvents such as dimethylformamide, dimethylacetamide, etc.; alcohols such as benzyl alcohol, methylbenzyl alcohol, etc.; ketones such as dipropyl ketone, dibutyl ketone, cyclohexanone, etc.; and esters such as methyl benzoate, propyl benzoate, isobutyl butyrate, etc.

Appropriate heating temperature is 100°–200° C. No active catalyst is obtained below 100° C., and a catalyst having a low activity is obtained above 200° C.

Heating time is 30 minutes or longer, and preferably 1–3 hours. No catalyst having a high activity is obtained for s shorter time, and the activity etc. are not improved for a longer time, though there is no harm.

If there is oxygen gas at the heating, no active catalyst is obtained. Therefore, the air must be replaced with other gas. Appropriate other gas includes, helium, hydrogen, carbon monoxide, nitrogen, argon, methane, etc.

The catalyst is produced by dissolving dicobalt octacarbonyl and an aromatic nitrile into a solvent at first and then heating the solution as described above. Since solubilities of dicobalt octacarbonyl and aromatic nitrile depend upon the kind of solvent, the proportion of aromatic nitrile to dicobalt octacarbonyl must be appropriately selected in view of the solvent. Usually, 0.5–50 moles of aromatic nitrile is used per mole of dicobalt octacarbonyl. To use the aromatic nitrile in excess is not objectionable, but not advantageous becauuse of an increased amount of the solvent.

It is needless to say that the precipitate formed by heating dicobalt octacarbonyl together with an aromatic nitrile in a solvent can be used as it is as a catalyst for the hydrogenation of nitriles, and if necessary, the precipitate can be separated from solvent and dried. The catalyst thus produced can be handled stably in the presence of air and can directly be used for the hydrogenation reaction. The catalyst once dried can be handled stably in the presence of air at the ordinary temperature, though the drying must be carried out in a system containing no air when it is dried with heating.

Though the catalyst can be used alone, it may also be used after mixing with diatomaceous earth, etc. and shaping.

The catalyst thus prepared is stable even if handled in the air, and can directly be used for the hydrogenation of nitriles without need of reduction with hydrogen in advance.

The catalyst of the present invention has a high activity in the hydrogenating of nitriles to form amines, and is applicable to aliphatic and aromatic nitriles having one or more cyano groups. Of course, the nitriles may have other substitutents inert to the hydrogenation. Examples of said nitriles include acetonitrile, propionitrile, adiponitrile, benzonitrile, m-tolunitrile, isophthalonitrile, terephthalonitrile, acetone cyanhydrin, etc. Though the hydrogenation conditions cannot be defined generally because they depend upon starting material, but a temperature of 50°–200° C. under a pressure of 50 kg/cm$^2$ gage or more in the presence of ammonia for the prevention of secondary amine formation is appropriate.

The catalyst of the present invention not only exhibits a high activity in the hydrogenation of nitriles, but also is stable even if handled in the air in the form as prepared and can be used as it is without reduction with hydrogen in advance.

EXAMPLES 1-3

0.76 g of dicobalt octacarbonyl, 0.3 g of various aromatic nitriles and 20 ml of m-xylene as a solvent were charged into a 100 ml eggplant type flask equipped with a reflux condenser and a gas inlet tube, and the air was thoroughly replaced while introducing nitrogen through the gas inlet tube. Thereafter, the flask was heated in an oil bath and the temperature of oil bath was elevated to 160° C. The flask was heated for 90 minutes under reflux conditions while passing nitrogen therethrough, and then the heating was discontinued and the flask was cooled to room temperature. The precipitate formed was directly transferred into a shaking type autoclave having a net capacity of 100 ml together with solvent m-xylene. After adding 10 g of isophthalonitrile and 10 ml of m-xylene thereto, the gas in the autoclave was replaced with nitrogen. After adding 10 ml of liquid ammonia thereto, hydrogen was fed up to a pressure of 260 kg/cm$^2$ gage and the hydrogenation of isophthalonitrile was carried out at a reaction temperature of 100° C. until no absorption of hydrogen took place. The m-xylenediamine thus formed was analyzed by gas chromatography, the results as shown in Table 1 were obtained.

TABLE 1

|  | Aromatic nitrile used in catalyst production | Time required for hydrogenation reaction (min.) | Yield of m-xylenediamine (%) |
| --- | --- | --- | --- |
| Example 1 | Isophthalonitrile | 90 | 92.2 |
| Example 2 | Terephthalonitrile | 180 | 80.6 |
| Example 3 | Benzonitrile | 215 | 81.0 |

EXAMPLE 4

In the procedure of Example 1, the precipitate formed by the heating was collected by filtration and washed with m-xylene until isophthalonitrile became undetectable in the filtrate. Then, the precipitate was transferred into a 100 ml autoclave, and 10 g of isophthalonitrile, 30 ml of m-xylene and 10 ml of liquid ammonia were added thereto, and the isophthalonitrile was hydrogenated at 100° C. under an initially charged hydrogen pressure of 260 kg/cm$^2$ gage. The reaction was completed in 85 minutes, and m-xylylenediamine was obtained in a yield of 96.5%.

EXAMPLE 5

In the procedure of Example 4, the filtered and washed precipitate was further washed with ethyl ether and then vacuum-dried, whereby 0.22 g of a black colored powder was obtained. The powder was left standing in the air for about 2 weeks, and then 10 g of isophthalonitrile was hydrogenated under the same conditions as in Example 4 by using the powder as a catalyst. The reaction was completed in 120 minutes, and the yield of m-xylenediamine was 95.6%.

EXAMPLES 6-13

Catalysts were prepared in the same manner as in Example 1, while the weight ratio of isophthalonitrile to dicobalt octacarbonyl, the concentration of dicobalt octacarbonyl in the solvent m-xylene, the temperature of heat treatment and the time of heating in the preparation of catalyst were changed in various manners. In the presence of these catalysts, hydrogenation of isophthalonitrile was carried out at 100° C. under an initially charged hydrogen pressure of 260 kg/cm$^2$ gage. The conditions of catalyst preparation, the conditions of hydrogenation of isophthalonitrile and the results obtained are summarized in Table 2, wherein "iPN" means isophthalonitrile.

TABLE 2

| | Conditions of catalyst preparation | | | | | Hydrogenation conditions of iPN | | | Results obtained | |
| --- | --- | --- | --- | --- | --- | --- | --- | --- | --- | --- |
| Example | Co$_2$(CO)$_8$ (g) | iPN (g) | m-Xylene (ml) | Temperature (°C.) | Time (min.) | Additional iPN (g) | Additional m-xylene (ml) | Liquid ammonia (ml) | Time required for the reaction (min.) | Yield of m-xylenediamine (%) |
| 6 | 0.76 | 5 | 20 | 160 | 210 | 5 | 10 | 10 | 65 | 93.7 |
| 7 | " | 1 | " | " | 90 | 9 | " | " | 80 | 94.9 |
| 8 | " | " | 10 | " | " | " | 20 | " | 120 | 86.4 |
| 9* | " | " | 60 | " | " | | | | 60 | 95.4 |
| 10 | " | " | 20 | " | " | 9 | 10 | 10 | 80 | 94.9 |
| 11 | " | " | " | 135 | " | " | " | " | 135 | 95.6 |
| 12 | " | 5 | " | 160 | " | 0 | " | " | 55 | 93.2 |
| 13 | " | " | " | " | 210 | 0 | " | " | 64 | 94.1 |

*After filtering the resulting precipitate, hydrogenation was carried out with the precipitate by using 9 g of iPN, 30 ml of m-xylene and 10 ml of liquid ammonia.

EXAMPLE 14

0.76 g of dicobalt octacarbonyl, 1 g of isophthalonitrile and 20 ml of m-xylene were charged into a 100 ml eggplant type flask equipped with a reflux condenser and a gas inlet tube and the air in the flask was thoroughly replaced while introducing carbon monoxide through the gas inlet tube. Thereafter, the flask was heated in an oil bath at 160° C. for 90 minutes under reflux while passing carbon monoxide therethrough. After the heating, the flask was cooled to room temperature and the resulting precipitate was directly transferred into a 100 ml shaking type autoclave together with solvent m-xylene. After adding 9 g of isophthalonitrile and 10 ml of m-xylene thereto, the gas in the autoclave was replaced with hydrogen. Further 10 ml of liquid ammonia was added thereto and the isophthalonitrile was hydrogenated at a reaction temperature of 100° C. under an initially charged hydrogen pressure of 260 kg/cm$^2$ gage. The reaction was completed in 120 minutes and m-xylenediamine was obtained in a yield of 96.4%.

EXAMPLE 15

In the procedure of Example 14, the catalyst was prepared by using hydrogen in place of carbon monoxide. The catalyst was collected by filtration, and 9 g of isophthalonitrile, 30 ml of m-xylene and 10 ml of liquid ammonia were added thereto, and the isophthalonitrile was hydrogenated at a temperature of 100° C. under an initially charged hydrogen pressure of 260 kg/cm² gage. The reaction was completed in 135 minutes, and the yield of m-xylenediamine was 95.4%.

EXAMPLE 16

1 g of isophthalonitrile and 30 ml of m-xylene were charged into a 300 ml three-necked separable flask equipped with a reflux condenser, a dropping funnel and a gas inlet tube, and the air in the falsk was thoroughly replaced with introduced nitrogen through the gas inlet tube. Thereafter, while stirring the flask with a magnetic rotor in an oil bath, the temperature of mother liquor was adjusted to 100° C. At the temperature of mother liquor of 100° C., a solution of 0.76 g of dicobalt octacarbonyl in 30 ml of m-xylene was dropped through the dropping funnel over about 10 minutes. After the dropwise addition, the temperature of oil bath was elevated to 160° C. and a heating was carried out for 90 minutes under reflux. After the heating, the mixture was cooled to room temperature and the resulting precipitate was collected by filtration and washed with m-xylene until isophthalonitrile became undetectable in the filtrate. In the presence of the precipitate thus prepared, hydrogenation of isophthalonitrile was carried out with 30 ml of m-xylene, 10 ml of liquid ammonia and 9 g of isophthalonitrile at 100° C. under an initially charged hydrogen pressure of 260 kg/cm² gage. The reaction was completed in 55 minutes, and the yield of m-xylenediamine was 94.8%.

EXAMPLES 17-19

In the presence of the precipitate prepared in the same manner as in Example 4, various nitriles were hydrogenated with 30 ml of m-xylene and 10 ml of liquid ammonia at a temperature of 100° C. under an initially charged hydrogen pressure of 260 kg/cm² gage. The results obtained are summarized in Table 3.

TABLE 3

| Example | Nitrile used in catalyst production (g) | Time required for hydrogenation reaction (min.) | Product | Yield (%) |
|---|---|---|---|---|
| 17 | Terephthalonitrile 10 | 80 | p-Xylenediamine | 84.9 |
| 18 | Benzonitrile 10 | 55 | Benzylamine | 99.8 |
| 19 | Adiponitrile 9.8 | 130 | Hexamethylenediamine | 98.5 |

EXAMPLE 20

Terephthalonitrile was hydrogenated in the same manner as in Example 17, except that, in the preparation of catalyst, the precipitate was prepared by using terephthalonitrile in place of the isophthalonitrile. The reaction was completed in 67 minutes, and the yield of p-xylenediamine was 90.1%.

EXAMPLE 21

30 ml of m-xylene, 1 g of isophthalonitrile and 5 g of diatomaceous earth were charged into a 300 ml three-necked separable flask equipped with a reflux condenser, a dropping funnel and a gas inlet tube, and the air in the flask was thoroughly replaced with nitrogen introduced through the gas inlet tube. Thereafter, while stirring the flask with a magnetic rotor, a solution of 2.28 g of dicobalt octacarbonyl in 30 ml of m-xylene was added at once through the dropping funnel. After adding the solution of dicobalt octacarbonyl thereto, the separable flask was dipped in an oil bath and the temperature of the bath was elevated to 160° C. The mixture was heated for 90 minutes under reflux while passing nitrogen therethrough, and then was cooled to room temperature, and the precipitate was collected by filtration. The precipitate was washed with m-xylene until isophthalonitrile became undetectable in the filtrate, further washed with ethyl ether and then vacuum-dried to obtain 5.52 g of a catalyst supported on diatomaceous earth. In the presence of 1.67 g of the catalyst supported on diatomaceous earth, hydrogenation of isophthalonitrile was carried out with 10 g of isophthalonitrile, 30 ml of m-xylene and 10 ml of liquid ammonia at 100° C. under an initially charged hydrogen pressure of 260 kg/cm² gage. The reaction was completed in 120 minutes, and the yield of m-xylenediamine was 94.9%.

EXAMPLE 22

A precipitate was prepared in the same manner as in Example 7, except that the m-xylene was replaced by mesitylene and the temperature of oil bath was adjusted to 180° C. The resulting precipitate was directly transferred into a 100 ml autoclave together with the solvent mesitylene, and 9 g of isophthalonitrile and 10 ml of mesitylene were added thereto, and then the gas in the autoclave was replaced with hydrogen. After adding 10 ml of liquid ammonia thereto, hydrogen was charged up to a pressure of 260 kg/cm² gage, and the isophthalonitrile was hydrogenated at a reaction temperature of 100° C. The reaction was completed in 78 minutes, and the yield of m-xylylenediamine was 94.1%.

EXAMPLE 23

The procedure of Example 12 was repeated, except that the hydrogenation of isophthalonitrile was carried out at an initially charged hydrogen pressure of 150 kg/cm² gage. The reaction was completed in 58 minutes, and the yield of m-xylylenediamine was 95.4%.

EXAMPLE 24

5.05 g of a catalyst supported on diatomaceous earth was prepared by repeating the procedure of Example 21, except that dicobalt octacarbonyl was used in an amount of 0.78 g. In the presence of 2.0 g of the catalyst, hydrogenation of isophthalonitrile was carried out with 10 g of isophthalonitrile, 30 ml of m-xylene and 10 ml of liquid ammonia at 100° C. under an initially charged hydrogen pressure of 260 kg/cm² gage. The reaction was completed in 370 minutes, and the yield; of m-xylylenediamine was 89.8%.

EXAMPLE 25

From the reaction product obtained in Example 6, the catalyst was recovered by centrifuge. In the presence of the recovered catalyst, hydrogenation of isophthalonitrile was carried out with 5 g of isophthalonitrile, 30 ml of m-xylene and 10 ml of liquid ammonia at 100° C. under an initially charged hydrogen pressure of 260 kg/cm² gage. The reaction was completed in 50 minutes, and the yield of m-xylylenediamine was 96.4%.

Comparative Example 1

10 g of isophthalonitrile, 0.76 g of dicobalt octacarbonyl and 30 ml of m-xylene were charged into a shaking type autoclave having a net capacity of 100 ml. After replacing the gas in the autoclave with hydrogen and adding 10 ml of liquid ammonia thereto, hydrogen was charged up to a pressure of 260 kg/cm² gage and the reaction was carried out at a reaction temperature of 200° C. for 6 hours. The yield of m-xylylenediamine was as low as 16.2%.

The same procedure as above was also carried out at a temperature of 100° C. No hydrogen was absorbed at all, and no reaction took place.

Comparative Example 2

58.2 g of cobalt nitrate was dissolved into 200 ml of water. 11.8 g of powdery diatomaceous earth was added thereto, and the mixture was kept at 70° C. While stirring the mixture thoroughly, a solution of 44.2 g of ammonium carbonate in 200 ml of water, prepared separately, was slowly added thereto dropwise over 90 minutes. The resulting mixture was stirred at that temperature for 3 hours and then allowed to stand for one hour for aging. The precipitate thus obtained was filtered and twice washed each with about 200 ml of water. After the washing, the precipitate was dried overnight in an air oven kept at 110° C., and then heated at a temperature elevation rate of 50° C./hr while introducing air thereto, and decomposed and fired at 380° C. for 3 hours. After the firing, it was transferred into a glass vessel, and the vessel was dipped in a niter bath. Hydrogen was slowly added thereto while passing nitrogen therethrough, and the temperature was made to elevate up to 420° C. at a temperature elevation rate of 50° C./hr, and then the gas was wholly replaced with hydrogen gas and the precipitate was reduced with hydrogen at that temperature for 3 hours. (After the reduction, the catalyst contained about 50% by weight of cobalt.) After completion of the reduction, the vessel was taken out of the nither bath and cooled to room temperature while passing hydrogen therethrough. After thorough replacement of the hydrogen with nitrogen, the catalyst was transferred together with 30 ml of m-xylene into a 100 ml shaking type autoclave. After adding 10 g of isophthalonitrile to the autoclave, the gas in the autoclave was replaced with hydrogen and then 10 ml of liquid ammonia was added thereto. Hydrogen was filled therein up to a pressure of 260 kg/cm² gage, and the reaction was carried out at a reaction temperature of 120° C. The reaction was completed in 180 minutes, and the yield of m-xylylenediamine was 75%. When the reaction was carried out at a temperature of 100° C., no reaction took place at all.

EXAMPLES 26–28

12.29 g of a catalyst supported on diatomaceous earth was prepared by repeating the procedure of Example 21, except that a solution of 5.92 g of isophthalonitrile in 70 ml of m-xylene and a solution of 15 g of cobalt octacarbonyl in 70 ml of m-xylene were used. In the presence of 0.62 g of this catalyst, 10 g of isophthalonitrile was hydrogenated with 30 ml of m-xylene and 10 ml of liquid ammonia at a reaction temperature of 100° C. under a constant pressure. The results obtained are shown in Table 4.

TABLE 4

| Example | Reaction pressure (kg/cm² gage) | Time required for reaction (min.) | Yield of m-xylylenediamine (%) |
|---|---|---|---|
| 26 | 160 | 172 | 96.7 |
| 27 | 100 | 270 | 95.1 |

On the other hand, in the presence of 0.62 g of the catalyst, 10 g of isophthalonitrile was hydrogenated with 30 ml of m-xylene and 10 ml of liquid ammonia at a reaction temperature of 150° C. at a constant volume under an initially charged hydrogen pressure of 260 kg/cm² gage. The reaction was completed in a few minutes and the yield of m-xylylenediamine was 97.5%. (Example 28)

EXAMPLE 29

A catalyst was prepared by repeating the procedure of Example 4, except that the m-xylene was replaced by ethyl benzoate and the temperature of heating was 190° C. In the presence of the catalyst, hydrogenation of isophthalonitrile was carried out. The reaction was completed in 150 minutes, and the yield of m-xylylenediamine was 92.7%.

Comparative Example 3

In the procedure of Example 7, a catalyst was prepared without using isophthalonitrile, and the hydrogenation of isophthalonitrile was carried out under the same conditions. In this case, no hydrogen was absorbed at all and no reaction took place.

EXAMPLE 30

11.85 g of a catalyst supported on MgO was prepared in the same manner as in Example 21 by using 10 g of MgO powder fired at 1,300° C. for 5 hours, a solution of 1.97 g of isophthalonitrile in 30 ml of m-xylene and a solution of 5 g of cobalt octacarbonyl in 30 ml of m-xylene. In the presence of 1.84 g of this catalyst, 10 g of isophthalonitrile was hydrogenated with 30 ml of m-xylene and 10 ml of liquid ammonia at a reaction temperature of 100° C. under an initially charged hydrogen pressure of 260 kg/cm² gage. The reaction was completed in 120 minutes, and the yield of m-xylylenediamine was 98.5%.

EXAMPLE 31

6.47 g of a catalyst supported on α-Al₂O₃ was prepared by repeating the procedure of Example 30, except that 5 g of powdery α-Al₂O₃ was used. The catalyst was mixed with 3% by weight of graphite and formed into pellets. The pellets having a size of 6 mm×6 mm thus obtained was split into eight pieces. In the presence of 0.97 g of the pieces, 10 g of isophthalonitrile was hydrogenated under the same conditions as in Example 30. The reaction was completed in 190 minutes, and the yield of m-xylylenediamine was 97.2%.

What is claimed is:

1. A process for producing a catalyst for hydrogenation of nitriles, which comprises heating dicobalt octacarbonyl together with an aromatic nitrile at a temperature of 100°–200° C. in the absence of oxygen gas.

2. A process according to claim 1, wherein the aromatic nitrile is benzonitrile, phthalonitrile, isophthalonitrile, or terephthalonitrile.

3. A process according to claim 1, wherein a solvent capable of dissolving dicobalt octacarbonyl and the aromatic nitrile, and having a boiling point of 100° C. or higher is used.

4. A process according to claim 3, wherein the solvent is toluene, xylene, mesytylene, dimethylformamide, dimethylacetamide, benzyl alcohol, methylbenzyl alcohol, dipropylketone, dibutylketone, cyclohexanone, methyl benzoate, propyl benzoate, or isobutyl butyrate.

5. A process according to claim 1, wherein the heating is carried out for at least 30 minutes.

6. A process according to claim 5, wherein the heating is carried out for 1 to 3 hours.

7. A process according to claim 1, wherein 0.5-50 moles of the aromatic nitrile is used per mole of the dicobalt octacarbonyl.

8. The catalyst prepared according to any of claims 1 to 7.

* * * * *